(12) United States Patent
Dochnahl et al.

(10) Patent No.: US 8,288,563 B2
(45) Date of Patent: Oct. 16, 2012

(54) PROCESS FOR THE PREPARATION OF PYRAZOLE DERIVATIVES

(75) Inventors: Maximilian Dochnahl, Mannheim (DE); Martin Sukopp, Mannheim (DE); Alexander Korte, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/256,564

(22) PCT Filed: Mar. 12, 2010

(86) PCT No.: PCT/EP2010/053146
§ 371 (c)(1),
(2), (4) Date: Sep. 14, 2011

(87) PCT Pub. No.: WO2010/105969
PCT Pub. Date: Sep. 23, 2010

(65) Prior Publication Data
US 2012/0004421 A1    Jan. 5, 2012

(30) Foreign Application Priority Data
Mar. 16, 2009    (EP) .................................... 09155198

(51) Int. Cl.
*C07D 231/10*    (2006.01)
(52) U.S. Cl. .................................... 548/371.7
(58) Field of Classification Search ................ 548/371.7
See application file for complete search history.

(56) References Cited

U.S. PATENT DOCUMENTS

| 4,824,960 | A | 4/1989 | Gallenkamp et al. |
| 2011/0172436 | A1 | 7/2011 | Wolf et al. |
| 2011/0190510 | A1 | 8/2011 | Sukopp et al. |

FOREIGN PATENT DOCUMENTS

| DE | 3612939 | 10/1987 |
| WO | WO 98/39302 | 9/1998 |
| WO | WO 99/54288 | 10/1999 |
| WO | WO 2004/005245 | 1/2004 |
| WO | WO 2009/077590 | 12/2008 |
| WO | WO 2009/135808 | 5/2009 |
| WO | WO 2010/037693 | 4/2010 |

OTHER PUBLICATIONS

International Search Report prepared in International Application No. PCT/EP2010/053146, filed Mar. 12, 2010.
International Preliminary Report on Patentability from corresponding International Application No. PCT/EP2010/053146, filed Mar. 12, 2010.
Blomquist, A.T. et al., "Unsaturated nitriles as dienophiles in the diene synthesis", J. Org. Chem., (1945), pp. 149-158, vol. 149.
Markwalder, J. et al., "Synthesis and biological evaluation of 1-Aryl-4,5-dihydro-1*H*-pyrazolo[3,4-*d* ]pyrimidin-4-one inhibitors of cyclin-dependent kinases", J. Med. Chem., (2004), pp. 5894-5911, vol. 47.

Saggiomo, A., "The dinitriles of acetylenedicarboxylic and polyacetylenedicarboxylic acids.[1]", J. Org. Chem., (1957), pp. 1171-1175, vol. 22.

*Primary Examiner* — Joseph K. McKane
*Assistant Examiner* — Samantha Shterengarts
(74) *Attorney, Agent, or Firm* — Brinks Hofer Gilson & Lione

(57) ABSTRACT

The present invention refers to a process for the preparation of pyrazole derivatives of formula (I)

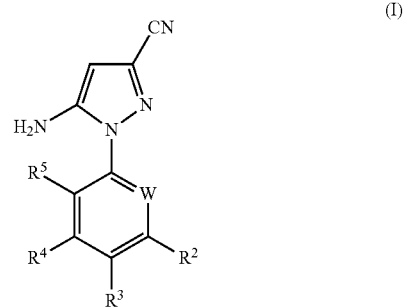

(I)

wherein W is nitrogen or $CR^1$, $R^1$, $R^2$, $R^4$ and $R^5$ are each independently selected from hydrogen, halogen, $C_1$-$C_6$-alkyl, $C_1$-$C_6$-haloalkyl, $C_1$-$C_6$-alkoxy, $C_1$-$C_6$-haloalkoxy, $R^7S(O)n$, nitro, cyano, and pentafluorothio; $R^3$ is hydrogen, halogen, $C_1$-$C_6$-alkyl, $C_1$-$C_6$-haloalkyl, $C_1$-$C_6$-alkoxy, $C_1$-$C_6$-haloalkoxy, $R^7S(O)n$, nitro, cyano, pentafluorothio or phenyl which is unsubstituted or substituted by 1 to 5 members of the group consisting of halogen, $C_1$-$C_6$-alkyl, $C_1$-$C_6$-haloalkyl, $C_1$-$C_6$-alkoxy, $C_1$-$C_6$-haloalkoxy, $R^7S(O)n$, nitro, cyano, and pentafluorothio which are the same or different; $R^7$ is $C_1$-$C_6$-alkyl or $C_1$-$C_6$-haloalkyl; and n is 0, 1, or 2; characterized in that hydrazines of formula (II)

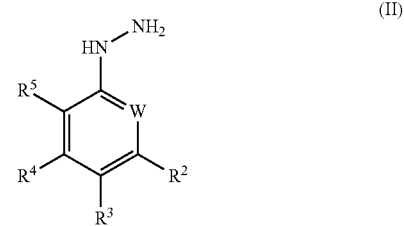

(II)

wherein W, $R^2$, $R^3$, $R^4$, and $R^5$ are as defined for pyrazole derivatives of formula (I), are reacted with a compound of formula (III)

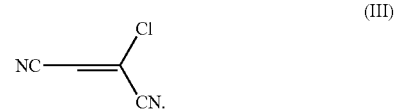

(III)

10 Claims, No Drawings

PROCESS FOR THE PREPARATION OF PYRAZOLE DERIVATIVES

This application is a National Stage application of International Application No. PCT/EP2010/053146, filed Mar. 12, 2010, the entire contents of which is hereby incorporated herein by reference. This application also claims priority under 35 U.S.C. §119 to European Patent Application No. 09155198.6, filed Mar. 16, 2009, the entire contents of which is hereby incorporated herein by reference.

The present invention relates to a novel process for the preparation of pyrazole derivatives of formula (I),

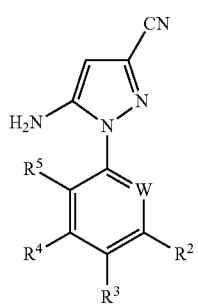

wherein
W is nitrogen or $CR^1$
$R^1$, $R^2$, $R^4$ and $R^5$ are each independently selected from hydrogen, halogen, $C_1$-$C_6$-alkyl, $C_1$-$C_6$-haloalkyl, $C_1$-$C_6$-alkoxy, $C_1$-$C_6$-haloalkoxy, $R^7S(O)n$, nitro, cyano, and pentafluorothio;
$R^3$ is hydrogen, halogen, $C_1$-$C_6$-alkyl, $C_1$-$C_6$-alkoxy, $C_1$-$C_6$-haloalkoxy, $R^7S(O)n$, nitro, cyano, pentafluorothio or phenyl which is unsubstituted or substituted by 1 to 5 members of the group consisting of halogen, $C_1$-$C_6$-alkyl, $C_1$-$C_6$-haloalkyl, $C_1$-$C_6$-alkoxy, $C_1$-$C_6$-haloalkoxy, $R^7S(O)n$, nitro, cyano, and pentafluorothio which are the same or different;
$R^7$ is $C_1$-$C_6$-alkyl or $C_1$-$C_6$-haloalkyl; and
n is 0, 1, or 2;
characterized in that hydrazines of formula (II)

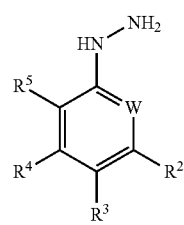

wherein W, $R^2$, $R^3$, $R^4$, and $R^5$ are as defined for pyrazole derivatives of formula (I), are reacted with a compound of formula (III)

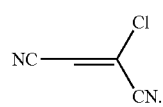

The resulting pyrazoles (I) are important intermediates in the production of pesticidally active 5-amino-1-phenyl-3-cyano-pyrazole derivatives. One especially important 5-amino-1-phenyl-3-cyano-pyrazole derivative is the market insecticide fipronil.

One way to prepare some pyrazoles of formula (I) from the respective hydrazines has inter alia been described in WO 98/39302. According to the teaching of this document, in a first step, hydrazines are reacted with fumaronitrile (trans-CN—CH═CH—CN) to give the intermediate 2-arylhydrazinosuccinonitriles. These 2-arylhydrazinosuccinonitriles in a second step can be oxidized to 2-arylhydrazonosuccinonitriles followed by, in a third step, cyclization, in order to yield pyrazoles of formula (I).

This reaction sequence has several disadvantages:
(a) it consists of three steps, associated with considerable investment for potential scale up for technical manufacture of the product;
(b) the yield of the first step and thus the overall yield is poor (according to the examples only 45 to 63 percent for the first step);
(c) the preferred oxidizing agents for the second step are transition metal salts which are difficult to remove from the reaction product to the extent to comply with registration requirements of agrochemical products such as fipronil.

WO 99/54288 aims at preparing open-chain 3-arylhydrazonopropionitriles from hydrazines. The former can then be optionally derivatized and inter alia transformed into 5-aminopyrazoles. This transformation requires three additional reaction steps:
(a) the addition of HCN to introduce a cyano group into the chain, yielding 2-arylhydrazinosuccinonitriles compounds, followed by
(b) oxidation to the cyano-substituted 2-arylhydrazonosuccinonitriles and
(c) cyclization to give the pyrazoles.

This four-step process to pyrazoles of formula (I) is unfavorable especially with regard to its poor yield as, for example, the reaction with HCN works with only about 40 percent yield.

DE 3612939 teaches a two-step synthesis of derivatives of pyrazoles which in contrast to the pyrazoles of formula (I) do not carry a cyano group in the 3-position of the pyrazole ring. This two-step synthesis involves reacting hydrazines with $CH_2$═CH—CN in a first step and oxidation plus cyclization in the presence of a base in a second step. There is no suggestion or teaching (a) how the oxidation step could be avoided and (b) how the cyano group could be introduced at the 3-position of the pyrazole ring.

WO 04/005245 is directed to the preparation of derivatives of maleonitrile and fumaronitrile, with an aim to reduce the number of synthetic steps needed to arrive at 4-sulphenylated 5-aminopyrazoles from hydrazines. Also, in example 1, a one-step synthesis of a 5-amino-3-cyano pyrazole derivative from the respective hydrazine with dicyanoacetylene is described. Although the yield of this step is satisfying, the preparation of the reactant dicyanoacetylene is generally accompanied by low yields, and requires very low temperatures and precautionary matters against explosion (see e.g. J. Org. Chem. 1945, 10, p. 149, and J. Org. Chem. 1957, 22, p. 1171). This is very unfavorable with regard to possible scale-up.

It was an object of the present invention to provide a new and improved preparation process of pyrazole compounds (I). Specifically, it was an object to provide a new and improved preparation process of pyrazole compounds (I) which involves a reduced number of synthetic steps. Moreover, it was an object to provide a new and improved preparation process of pyrazole compounds (I) with an increased overall yield. It was also an object to provide a new and improved preparation process of pyrazole compounds (I) which process employs readily available starting materials.

Accordingly, the inventive process defined at the outset was found. Surprisingly, the reaction of the hydrazine derivatives (II) with compounds (III) gave the desired pyrazole derivatives (I) in a one-step process with excellent overall yield.

Compounds (III) may be used in the form of the cis-isomer (chloromaleonitrile) or of the trans-isomer (chlorofumaronitrile), or of mixtures thereof. With regard to the inventive process, the use of a mixture of chloromaleonitrile and chlorofumaronitrile is preferred.

The substituents have the following meanings:

The term halogen denotes in each case fluorine, bromine, chlorine or iodine, in particular fluorine, chlorine or bromine, preferably chlorine or fluorine.

The term "$C_1$-$C_6$-alkyl" as used herein refers to a saturated straight-chain or branched hydrocarbon group having 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyland their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "$C_1$-$C_6$-alkoxy" as used herein refers to a straight-chain or branched saturated alkyl group having 1 to 6 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_6$-haloalkoxy" as used herein refers to a $C_1$-$C_6$-alkoxy group as mentioned above wherein the hydrogen atoms are partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

With regard to the inventive process, the substituents of compounds of formulae (I) and (II) preferably have the following meanings:

W is nitrogen or $CR^1$, preferably $CR^1$.

$R^1$ and $R^5$ are preferably selected from hydrogen, halogen, $C_1$-$C_6$-alkyl, $C_1$-$C_6$-haloalkyl, more preferably from halogen and $C_1$-$C_4$-haloalkyl, even more preferably from chlorine, fluorine and trifluoromethyl, most preferably from chlorine.

$R^2$ and $R^4$ preferably are hydrogen.

$R^3$ preferably is halogen, $C_1$-$C_6$-alkyl, $C_1$-$C_6$-haloalkyl, $C_1$-$C_6$-alkoxy, $C_1$-$C_6$-haloalkoxy, or pentafluorothio, more preferably $C_1$-$C_6$-alkyl, $C_1$-$C_6$-haloalkyl or pentafluorothio, even more preferably $C_1$-$C_4$-haloalkyl, and most preferably trifluoromethyl.

Further preferred substituents are:
W is nitrogen or $CR^1$
$R^1$ and $R^5$ are each independently selected from hydrogen, halogen, $C_1$-$C_4$-alkyl, and $C_1$-$C_4$-haloalkyl;
$R^2$ and $R^4$ are hydrogen; and
$R^3$ is halogen, $C_1$-$C_4$-alkyl, $C_1$-$C_4$-haloalkyl, or pentafluorothio.

Most preferably, the substituents of compounds of formulae (I) and (II) have the following meanings:
W is C—Cl
$R^1$ and $R^5$ are halogen, preferably chlorine;
$R^2$ and $R^4$ are hydrogen; and
$R^3$ is $C_1$-$C_4$-haloalkyl, preferably trifluoromethyl.

In an especially preferred embodiment, a process for the preparation of 5-amino-1-(2,6-dichloro-4-trifluoromethylphenyl)-1H-pyrazole-3-carbonitrile by reaction of compounds (III) with (2,6-dichloro-4-trifluoromethylphenyl)-hydrazine is provided.

The reaction preferably is conducted in the presence of an inorganic or organic base.

Suitable inorganic bases are, for example, alkali metal and alkaline earth metal hydroxyides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate. Preferred inorganic bases are alkoxides of alkali metals or earth alkali metals. In a more preferred embodiment the inorganic base is chosen from sodium or potassium methoxide or ethoxide. Most preferably, sodium methoxide is used.

When the base is an inorganic base, preferably alcohols are used as solvents.

The base may also be a Lewis base, such as tri-n-butylphosphine, triphenylphosphine, triphenylphosphinoxide or triethylphosphite, preferably triphenylphosphineoxide.

Preferably, the base is an organic base.

The organic base advantageously is an amine base, i.e. a base wherein the site of basicity is a nitrogen atom.

Preferably, the amine base is secondary or tertiary alky-, alkenyl-, or alkinylamine or an arylamine or a heterocyclic aromatic amine. More preferably, the amine base is tertiary alky-, alkenyl-, or alkinylamine or an arylamine or a heterocyclic aromatic amine.

"Alkylamine" herein is defined as a nitrogen atom which carries 1, 2 or 3 straight-chain or branched alkyl groups having 1 to 10 carbon atoms which may be the same or different.

"Alkenylamine" herein is defined as a nitrogen atom which carries 1, 2 or 3 straight-chain or branched alkenyl groups having 2 to 10 carbon atoms which may be the same or different.

"Alkinylamine" herein is defined as a nitrogen atom which carries 1, 2 or 3 straight-chain or branched alkinyl groups having 2 to 10 carbon atoms which may be the same or different.

Alkyl groups having 1 to 10 carbon atoms are branched or unbranched saturated hydrocarbon groups having 1 to 10 carbon atoms, such as, and preferably, $C_1$-$C_6$-alkyl, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Alkenyl groups having 2 to 10 carbon atoms are linear or branched unsaturated hydrocarbon groups having 2 to 10 carbon atoms and a double bond in any position, such as, and preferably, $C_2$-$C_6$-alkenyl, for example ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkinyl groups having 2 to 10 carbon atoms are linear or branched unsaturated hydrocarbon groups having 2 to 10 carbon atoms and a triple bond in any position, such as, and preferably, $C_2$-$C_6$-alkinyl, for example ethinyl, 1-propinyl, 2-propinyl, 1-butinyl, 2-butinyl, 3-butinyl, 1-pentinyl, 2-pentinyl, 3-pentinyl, 4-pentinyl, 1-hexinyl, 2-hexinyl, 3-hexinyl, 4-hexinyl, and 5-hexinyl.

The alkyl or alkenyl groups together with the nitrogen atom to which they are attached may form an unsaturated or partially unsaturated cyclic or bicyclic 3 to 10-membered ring system which besides the nitrogen atom may contain 1 to 3 further heteroatoms selected from oxygen, nitrogen or sulfur, preferably from nitrogen, such as pyrrolidine, piperidine, morpholine, piperazine, DABCO (1,4-diazabicyclo[2.2.2]octane), DBU (1,8-diazabicyclo[5.4.0]undec-7-ene), or DBN (1,5-diazabicyclo[4.3.0]non-5-ene), most preferably bicyclic ring systems such as DBU (1,8-diazabicyclo[5.4.0]undec-7-ene) and DBN (1,5-diazabicyclo[4.3.0]non-5-ene).

These alkyl, alkenyl or alkinyl groups including the cyclic or bicyclic ring systems may be further substituted by 1 to 5 groups selected from halogen, hydroxy, $C_1$-$C_6$-alkyl, $C_1$-$C_6$-haloalkyl, $C_1$-$C_6$-alkoxy, $C_1$-$C_6$-haloalkoxy, and di($C_1$-$C_6$-alkyl)amine, or with phenyl, pyrididyl, 1-naphthyl, or 2-naphthyl, which aryl groups may be substituted by 1 to 3 groups selected from halogen, hydroxy, $C_1$-$C_6$-alkyl, $C_1$-$C_6$-haloalkyl, $C_1$-$C_6$-alkoxy, $C_1$-$C_6$-haloalkoxy, or di($C_1$-$C_6$-alkyl)amine.

"Arylamine" means a nitrogen atom which is substituted with at least one aryl group, especially with phenyl, biphenyl, pyrididyl, 1-naphthyl or 2-naphthyl groups which may be further substituted by 1 to 3 groups selected from halogen, hydroxy, $C_1$-$C_6$-alkyl, $C_1$-$C_6$-haloalkyl, $C_1$-$C_6$-alkoxy, $C_1$-$C_6$-haloalkoxy, and di($C_1$-$C_6$-alkyl)amine.

Heterocyclic aromatic amines are aromatic 5- to 10-membered mono- and bicyclic ring systems which beside the amine base nitrogen atom may contain 1 to 3 heteroatoms selected from oxygen, nitrogen, sulfur, wherein at least 1 carbon atom must be incorporated in the ring system, such as: pyrrole, imidazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazol, indole, indazole, isoindole, benzimidazole, benzisoxazole, benzisothiazole, benzopyrazole, benzothiadiazole, benzotriazole, carbazole, pyridine, 4-(dimethylamino)pyridine, 2-picoline, 3-picoline, 4-picoline, 5-ethyl-2-methylpyridine, 2-ethylpyridine, 2,3-lutidine, 2,4-lutidine, 2,5-lutidine, 2,6-lutidine, 3,4-lutidine, 3,5-lutidine, 2,4,6-collidine, 2,3,5-collidine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,5-naphthyridine, 1,6-naphthyridine, 1,7-naphthyridine, 1,8-naphthyridin, phthalazine, pyridopyrimidine, purine or pteridine.

The heterocyclic aromatic amine bases preferably are unsubstituted but may be substituted with 1 to 3 groups selected from halogen, hydroxy, $C_1$-$C_6$-alkyl, $C_1$-$C_6$-haloalkyl, $C_1$-$C_6$-alkoxy, $C_1$-$C_6$-haloalkoxy, and di($C_1$-$C_6$-alkyl)amine, or with phenyl, biphenyl, pyrididyl, 1-naphthyl, or 2-naphthyl, which aryl groups may be substituted by 1 to 3 groups selected from halogen, hydroxy, $C_1$-$C_6$-alkyl, $C_1$-$C_6$-haloalkyl, $C_1$-$C_6$-alkoxy, $C_1$-$C_6$-haloalkoxy, or di($C_1$-$C_6$-alkyl)amine), preferably with $C_1$-$C_3$-alkyl.

Preferred heterocyclic aromatic amine bases are pyridine, 4-(dimethylamino)pyridine, 2-picoline, 3-picoline, 4-picoline, 5-ethyl-2-methylpyridine, 2-ethylpyridine, 2,3-lutidine, 2,4-lutidine, 2,5-lutidine, 2,6-lutidine, 3,4-lutidine, 3,5-lutidine, 2,4,6-collidine, 2,3,5-collidine, pyrimidine, pyrazine, piperazine, 1,3,5-triazine, quinoline, isoquinoline, N-methylimidazole and N-methylpyrazole.

More preferred heterocyclic aromatic amine bases are 2-picoline, 3-picoline, 4-picoline, 5-ethyl-2-methylpyridine, 2-ethylpyridine, 2,3-lutidine, 2,4-lutidine, 2,5-lutidine, 2,6-lutidine, 3,4-lutidine, 3,5-lutidine, 2,4,6-collidine and 2,3,5-collidine. Most preferred are bases selected from 2,6-lutidine and 2,4,6-collidine.

Preferably, the amine base is selected from secondary or tertiary amines (including heterocyclic aromatic amines), most preferably from tertiary amines (including heterocyclic aromatic amines). Also, preferably, the base is a tertiary amine base wherein the nitrogen atom carries no or only one substitutent selected from methyl or ethyl.

Preferred tertiary amine bases are, for example, trimethylamine, triethylamine, tripropylamine, triisopropylamine, N,N-diisopropylmethylamine, tributylamine, N,N-dimethylethylamine, N,N-diethylmethylamine, N,N-dimethylpropylamine, N,N-dimethylcyclohexylamine, N,N-dimethylbenzylamine, N,N-diisopropylethylamine, triethanolamine, N-methyldiethanolamine, N-ethyldiethanolamine, N-butyldiethanolamine, N,N-dimethylethanolamine, N,N-diethylethanolamine, DABCO (1,4-diazabicyclo[2.2.2]octane), DBU (1,8-diazabicyclo[5.4.0]undec-7-ene), DBN (1,5-diazabicyclo[4.3.0]non-5-ene), N,N-dimethylaniline, N,N-diethylaniline, N-methylpyrrolidine, N-methylpiperidine, N-methylmorpholine, or N-ethylmorpholine.

Even more preferred tertiary amine bases are, triethylamine, tripropylamine, triisopropylamine, N,N-diisopropylmethylamine, N,N-diisopropylethylamine, DABCO (1,4-diazabicyclo[2.2.2]octane), DBU (1,8-diazabicyclo[5.4.0]undec-7-ene) or DBN (1,5-diazabicyclo[4.3.0]non-5-ene).

Most preferred tertiary amine bases are N,N-diisopropylethylamine, DBU (1,8-diazabicyclo[5.4.0]undec-7-ene) or DBN (1,5-diazabicyclo[4.3.0]non-5-ene).

Also, preferably, the base is a sterically hindered base.

Sterically hindered bases are defined as having at least one secondary, tertiary or quaternary carbon atom directly bonded to one of their sites of basicity or compounds wherein the site of basicity is part of a double bond. Preferably, the sterically hindered base is a sterically hindered amine base, wherein the site of basicity is a nitrogen atom. Most preferably, the sterically hindered base is selected from the tertiary amines.

Also, in a very preferred embodiment the basic nitrogen atom is incorporated into an aromatic 6 or 10 electron π-system leading to a lower basicity of the nitrogen atom.

Most preferred are bases selected from the heterocyclic aromatic amines.

Mixtures of the above-mentioned bases can also be used.

Generally, the molar ratio of the compound of formula (II): base is from about 1:0.01 to about 1:10. Preferably, 0.5 to 7 molar equivalents of base relative to compounds (II) are used, more preferably 0.75 to 5 molar equivalents, and most preferably 1.0 to 2 molar equivalents are used. The base can also be used as a solvent.

The reaction can be conducted with hydrazine of formula (II)/compounds of formula (III) molar ratios of from 1:0.1 to 1:10. Preferably, 0.5 to 5 molar equivalents of compounds (III) are used. Most preferably, 1 to 2 molar equivalents of compounds (III) are used.

Compounds of formula (II) can be prepared as described in e.g. WO 08/113,660 and WO 08/113,661 and according to references cited therein. Compounds (III) can be prepared as described in the literature, e.g. as in U.S. Pat. No. 2,443,494.

The reaction generally is performed in a solvent. Suitable solvents preferably are selected from
- water;
- alcohols, e.g. methanol, ethanol, n-propanol, isopropanol, n-butanol, isobutanol and tert-butanol preferably methanol and ethanol, most preferably methanol;
- aliphatic, alicyclic or aromatic, optionally halogenated hydrocarbons such as aromatic organic hydrocarbons, e.g. toluene, xylene, trifluoromethylbenzene, benzene, nitrobenzene, monochlorobenzene, dichlorobenzene, and ethylbenzene, or aliphatic or alicyclic, optionally halogenated hydrocarbons such as pentane, hexane, heptane, cyclohexane, 1,2-dichloroethane, dichloromethane, trichloromethane (chloroform), carbon tetrachloride, preferably toluene and hexane, most preferably hexane.
- ethers, e.g. diethyl ether, diisopropyl ether, tert-butyl methyl ether, 1,4-dioxane, tetrahydrofuran, 2-methyltetrahydrofuran, cyclopentyl methyl ether or ethylene glycol dimethyl- or diethyl ether; preferably tetahydrofuran and tert-butyl methyl ether, most preferably THF;
- ketons, e.g. acetone or butanone, preferably acetone.
- nitriles, e.g. acetonitrile, propionitrile or benzonitrile; preferably acetonitrile.
- amides, e.g. N,N-dimethylformamide, N,N-dimethylacetamide, DMI (1,3-dimethyl-2-imidazolidinone), N-methylformanilid, N-methylformamide, N-methylpyrrolidone or hexamethylphosphoric acid triamide; preferably N,N-dimethylformamide and N-methylpyrrolidone, most preferably N-methylpyrrolidone.
- sulfoxides, e.g. dimethylsulfoxide; or mixtures thereof.

Preferred solvents are selected from alcohols, most preferably methanol.

Generally, the molar concentration of the reactants is from about 0.01 to about 10 mol/l. Preferably, concentrations of 0.1 to 5 mol/l are used, more preferably concentrations ranging from 0.2 to 2 mol/l, and most preferably, a concentration of 0.5 to 0.9 mol/l is used.

The reaction can optionally be carried out under an inert gas atmosphere, such as an argon or a nitrogen atmosphere.

It is advantageous to add the base in small portions.

Generally, it is advantageous to add compounds (III) to a premixed solution of the corresponding arylhydrazine and the base. Preferably, the corresponding starting materials are pre-dissolved or suspended, respectively, in the reaction solvent before addition to the reaction mixture.

The reaction temperature generally is from about −20° C. to 65° C., preferably from 0° C. to 40° C., most preferably from 10° C. to 25° C.

The reaction time depends upon the reaction temperature, the temperature control during the process, and the different reagents and solvents. The skilled artisan will be able to determine the appropriate reaction time in order to achieve the desired yield and purity by HPLC, TLC or GC. Typically, the reaction time will be about 2 to 24 hours, preferably 12 to 16 hours.

After completion of the reaction, 5-amino-1-(2,6-dichloro-4-trifluoromethyl-phenyl)-1H-pyrazole-3-carbonitrile can be isolated by employing conventional methods such as diluting the reaction mixture with water extracting compounds of formula (I) with an organic solvent such as ethylacetate, tert-butyl methyl ether or dichloromethane, washing the extract, e.g. with dilute acid such as 10% citric acid, concentrating the extract, crystallization of compounds of formula (I), and the like. The isolated compounds of formula (I) can be purified by a technique such as chromatography, recrystallization and the like, if necessary.

EXAMPLES

HPLCs were taken on a Hewlett Packard HP 1200, Chemstation, equipped with a J'Sphere ODS-H80, 4 m, 4.6×250 mm (YMC) column, eluent A: 90 wt.-% water+10 wt.-% acetonitrile, eluent B: 10 wt.-% water+90 wt.-% acetonitrile, flow: 0.85 ml/min, detection: 235 nm, gradient:

| time [min] | 0 | 2 | 17 | 25 | 35 |
|---|---|---|---|---|---|
| A [%] | 60 | 60 | 25 | 0 | 0 |
| B [%] | 40 | 40 | 75 | 100 | 100 |

Yields given below are in mol percent of isolated product with >95% purity.

Example 1

5-amino-1-(2,6-dichloro-4-trifluoromethyl-phenyl)-1H-pyrazole-3-carbonitrile (alternative nomenclature: "5-amino-1-(2,6-dichloro-4-trifluoromethyl-phenyl)-3-cyanopyrazole")

A 50 mL round-bottom flask was charged with (2,6-dichloro-4-trifluoromethyl-phenyl)-hydrazine (1.2 g, 4.84 mmol), 2,6-lutidine (0.57 g, 5.32 mmol, 1.1 equiv.) and methanol (10 mL). A mixture of chloromaleonitrile and chlorofumaronitrile (0.82 g, 7.29 mmol) was slowly added at 20-25° C. Stirring was continued for about 16 hours at that temperature. The solution was then concentrated at a pressure of 50 mbar. The residue was purified by flash column chromatography (silica, hexanes/EtOAc 100:0→70:30) to give the product as a off-white solid (1.1 g, 3.43 mmol, 71%), melting point: 117-118° C., $^1$H-NMR (360 MHz, CDCl$_3$): δ [ppm]=7.78 (d, 2H, J=0.4 Hz); 6.04 (s, 1H); 3.83 (bs, 2H), $^{13}$C-NMR (125 MHz, DMSO-d$_6$): δ [ppm]=150.0; 136.0; 135.9; 132.7 (q, J=34 Hz); 126.43; 126.42; 122.4 (q, J=273 Hz); 114.6; 90.8.

Comparative Example

In order to demonstrate the advantages of the inventive process, the yield of the following reaction as described in examples 1/2, 3 and 5 of WO 98/39302 was determined:

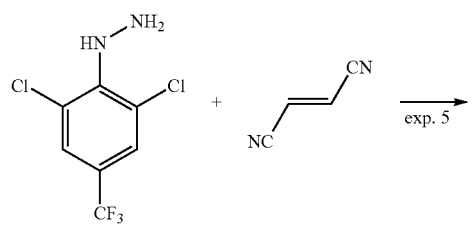

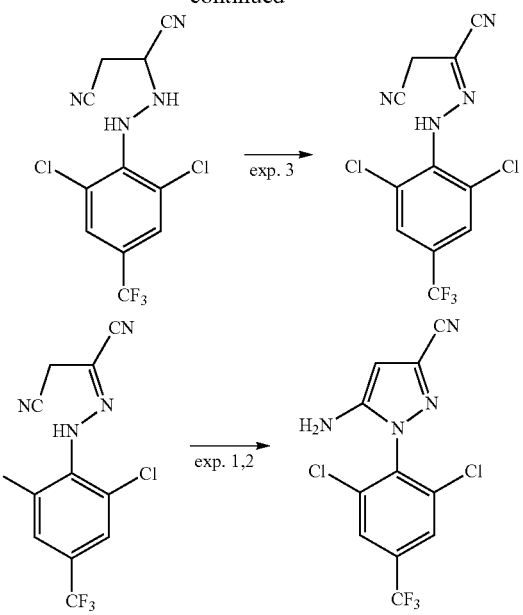

The overall yield of the pyrazole was 11 percent.

It was thus demonstrated that the inventive process gives much higher yields as compared to the processes described in WO 98/39302.

The invention claimed is:

1. A process for preparing a compound of formula (I),

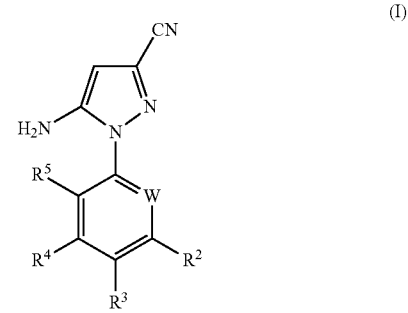

wherein

W is nitrogen or CR$^1$

R$^1$, R$^2$, R$^4$ and R$^5$ are each independently selected from the group consisting of hydrogen, halogen, C$_1$-C$_6$-alkyl, C$_1$-C$_6$-haloalkyl, C$_1$-C$_6$-alkoxy, C$_1$-C$_6$-haloalkoxy, R$^7$S(O)$_n$, nitro, cyano, and pentafluorothio;

R$^3$ is hydrogen, halogen, C$_1$-C$_6$-alkyl, C$_1$-C$_6$-alkoxy, C$_1$-C$_6$-haloalkoxy, R$^7$S(O)$_n$, nitro, cyano, pentafluorothio or phenyl which is unsubstituted or substituted by 1 to 5 members selected from the group consisting of halogen, C$_1$-C$_6$-alkyl, C$_1$-C$_6$-haloalkyl, C$_1$-C$_6$-alkoxy, C$_1$-C$_6$-haloalkoxy, R$^7$S(O)$_n$, nitro, cyano, and pentafluorothio which are the same or different;

R$^7$ is C$_1$-C$_6$-alkyl or C$_1$-C$_6$-haloalkyl; and n is 0, 1, or 2;

comprising reacting a compound of formula (II)

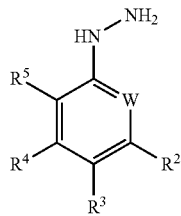

with a compound of formula (III)

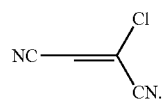

2. The process according to claim 1, wherein
W is $CR^1$;
$R^1$ and $R^5$ are each independently selected from halogen;
$R^2$ and $R^4$ are hydrogen; and
$R^3$ is $C_1$-$C_4$-haloalkyl.

3. The process according to claim 1, wherein
W is $CR^1$;
$R^1$ and $R^5$ are chloro;
$R^2$ and $R^4$ are hydrogen; and
$R^3$ is trifluoromethyl.

4. The process according to claim 3, wherein the reaction is conducted in the presence of an inorganic or organic base.

5. The process according to claim 4, wherein the reaction is conducted in the presence of an organic amine base.

6. The process according to claim 4, wherein the reaction is conducted in the presence of a sterically hindered organic amine base.

7. The process according to claim 4, wherein the process is conducted in the presence of a tertiary or heteroaromatic organic amine base.

8. The process according to claim 7, wherein the base is 2,6-lutidine or 2,4,6-collidine.

9. The process according to claim 2, wherein 0.01 to 10 molar equivalents of the organic base relative to hydrazines of formula (II) are used.

10. The process according to claim 1, wherein the reaction is conducted in a solvent at temperatures of from −20° C. to 65° C.

* * * * *

UNITED STATES PATENT AND TRADEMARK OFFICE
CERTIFICATE OF CORRECTION

PATENT NO. : 8,288,563 B2
APPLICATION NO. : 13/256564
DATED : October 23, 2012
INVENTOR(S) : Maximilian Dochnahl et al.

Page 1 of 1

It is certified that error appears in the above-identified patent and that said Letters Patent is hereby corrected as shown below:

Claim 1, col. 10, line 57, after "$C_1$-$C_6$-alkyl," insert --$C_1$-$C_6$-haloalkyl,--.

Signed and Sealed this
Fifth Day of February, 2013

Teresa Stanek Rea
*Acting Director of the United States Patent and Trademark Office*